:::
United States Patent [19]

Eastman

[11] 4,396,537
[45] Aug. 2, 1983

[54] PROMOTED COBALT CATALYST

[75] Inventor: Alan D. Eastman, Bartlesville, Okla.

[73] Assignee: Phillips Petroleum Company, Bartlesville, Okla.

[21] Appl. No.: 430,624

[22] Filed: Sep. 30, 1982

Related U.S. Application Data

[60] Division of Ser. No. 259,738, May 1, 1981, Pat. No. 4,368,346, which is a continuation-in-part of Ser. No. 181,515, Aug. 26, 1980, abandoned.

[51] Int. Cl.$^3$ .......................... B01J 27/14; B01J 27/06
[52] U.S. Cl. ..................................... 252/437; 252/435; 252/441
[58] Field of Search .................... 252/435, 437, 441

[56] References Cited

U.S. PATENT DOCUMENTS

| | | | |
|---|---|---|---|
| 3,248,432 | 4/1966 | Riley et al. | 252/437 X |
| 3,784,483 | 1/1974 | Cichowski | 252/437 |
| 3,790,500 | 2/1974 | Walker | 252/437 |
| 3,810,953 | 5/1974 | Cichowski | 252/437 X |
| 3,926,845 | 12/1975 | Cichowski | 252/437 X |
| 4,246,421 | 1/1981 | Bartek et al. | 252/437 |
| 4,260,520 | 4/1981 | Erpenbach et al. | 252/437 |

*Primary Examiner*—Delbert E. Gantz
*Assistant Examiner*—William G. Wright

[57] ABSTRACT

The catalytic oxidative dehydrogenation of paraffins having from 2 to 5 carbon atoms is carried out in the presence of a catalyst composition comprising cobalt; phosphorus; at least one promoter selected from the group consisting of zinc, titanium, zirconium, niobium, indium, lead and bismuth; and oxygen. The catalyst composition also comprises at least one alkali metal and/or at least one halogen selected from the group consisting of chlorine, bromine and iodine. The selectivity of the catalyst composition is improved by the presence of the at least one alkali metal. The conversion of the catalyst composition is improved by the presence of the at least one halogen.

6 Claims, No Drawings

PROMOTED COBALT CATALYST

This application is a division of application Ser. No. 259,738, filed May 1, 1981 now U.S. Pat. No. 4,368,346, which is a continuation-in-part of application Ser. No. 181,515, filed Aug. 26, 1980, now abandoned.

This invention relates to an improved catalytic process for the oxidative dehydrogenation of light paraffins, and a catalyst therefor.

Oxidative dehydrogenation processes for the conversion of paraffins to olefins are well known. Cobalt based catalysts are commonly used as the oxidative dehydrogenation catalyst. However, improving the selectivity of any catalyst composition is desirable and it is an object of this invention to provide a cobalt based catalyst composition which has an improved selectivity for the oxidative dehydrogenation of light paraffins and thus provides an improved process for the oxidative dehydrogenation of light paraffins.

In accordance with the present invention, a paraffin or mixtures of paraffins having from 2 to 5 carbon atoms is oxidatively dehydrogenated in the presence of a catalyst composition comprising cobalt; phosphorus; at least one promoter selected from the group consisting of zinc, titanium, zirconium, niobium, indium, lead and bismuth; and oxygen. At least one alkali metal may be added to the catalyst composition to improve the selectivity of the catalyst composition.

The conversion of the process may be improved by introducing a halogen at least periodically into the process. The improved conversion may also be obtained initially by using a compound containing a halogen to prepare the catalyst composition. If a halogen is introduced into the process, the catalyst composition will contain such halogen and will retain the halogen for a period of time after introduction of the halogen is terminated. The retention of the halogen for a period of time is a particularly advantageous feature of the catalyst composition.

In the process of the present invention, it is believed that the oxygen required for the oxidative dehydrogenation of the paraffin is supplied from the catalyst composition. Preferably, the oxidative dehydrogenation is carried out in a cyclic manner in which the catalyst composition is contacted alternately with a feed stream containing a light paraffin and a gaseous stream containing free oxygen. However, the oxidative dehydrogenation can be effected continuously by passing a feed stream containing a light paraffin plus free oxygen in contact with the catalyst composition under suitable oxidative dehydrogenation conditions.

If the catalyst composition is prepared using a compound containing a halogen, at least a part of the halogen will remain in the catalyst composition unless specific steps are taken to completely remove the halogen. The halogen remaining in the catalyst composition will improve the conversion of the process for a period of time (on the order of 15–25 cycles) but the beneficial effects of the halogen are soon lost because the halogen is removed as a volatile compound from the catalyst and does not remain in the process. The benefits of the halogen may be maintained by at least periodically introducing a halogen into the process. Such introduction insures the presence of a halogen in the catalyst composition and thus in the process and the benefits of the halogen are retained over a long period of time. Even if the introduction of the halogen is terminated for a period of time the halogen being volatilized from the catalyst composition will continue to provide a beneficial effect for a period of time and thus a periodic introduction of the halogen may be used.

Other objects and advantages of the invention will be apparent from the foregoing brief description of the invention and the appended claims as well as from the detailed description of the invention which follows.

Paraffins which can be oxidatively dehydrogenated in accordance with the present invention are paraffins which have from 2 to 5 carbon atoms per molecule. The oxidative dehydrogenation process of the present invention is particularly applicable to the conversion of ethane to ethylene.

The catalyst composition employed in the process of the present invention comprises cobalt; phosphorus; at least one promoter selected from the group consisting of zinc, titanium, zirconium, niobium, indium, lead and bismuth; and oxygen. The catalyst composition must also contain at least one alkali metal and/or at least one halogen. Sufficient oxygen is present in the catalyst composition to satisfy the valence requirements of the cobalt, phosphorus, the at least one promoter and the at least one alkali metal. If the halogen is present, the halogen will replace some oxygen.

The at least one alkali metal is selected from the group consisting of lithium, sodium, potassium, rubidium and cesium. The particularly preferred alkali metals are sodium and potassium.

The halogens which may be used in the process of the present invention comprise chlorine, bromine and iodine. The presently preferred halogen is chlorine.

The catalyst composition can be prepared by any suitable method. Preferably, soluble salts of cobalt and the promoter are combined in solution and coprecipitated with a suitable base to form a mixture of hydroxides, hydrous oxides, carbonates or other insoluble forms. The coprecipitate is then separated from the solution and phosphorus and at least one alkali metal, if used, are added in the quantity required. The phosphorus and alkali metal can be added as dry, powdered solids, as solutions of separate compounds or as a single compound, i.e., sodium phosphate or potassium phosphate. After the phosphorus and the at least one alkali metal are added to the catalyst composition, the composition is heated in the presence of free oxygen at a temperature high enough to convert the components of the catalyst composition to the oxide forms. Generally this temperature will range from about 450° C. to about 850° C.

If it is desired to initially incorporate a halogen into the catalyst composition, such halogens may be added by using a halogen containing salt of a compound used to prepare the catalyst. A halogen can also be added in the form of an ammonium halide.

The catalyst composition may also be prepared by mixing the catalyst components as dry powders or as wet paste in the oxide form or as compounds readily convertible to oxides by heating in the presence of oxygen. Water or concentrated aqueous ammonia are preferred wetting agents to form the wet paste. After the catalyst components are intimately mixed, the mixture is calcined in the presence of oxygen at a temperature in the range of about 450° C. to about 850° C. The calcination should continue for about 1 hour at the higher temperatures (750° C.–850° C.) with longer calcination periods being desirable at the lower temperatures.

If it is desired to incorporate a halogen into the catalyst composition using this second method of preparation, the catalyst composition may again be prepared by adding some catalyst components in the halide form. Also, an ammonium halide may be included in the mixture of catalyst components.

Any suitable atomic ratio of cobalt to the promoter may be utilized in the catalyst composition. Preferably the atomic ratio of cobalt to the metal promoter is in the range of about 1:1 to about 20:1 and is more preferably in the range of about 3:1 to about 6:1. Any suitable concentration of phosphorus may be utilized in the catalyst composition. Preferably the concentration of phosphorus is in the range of about 1 to about 10 weight percent and is more preferably in the range of about 2 to about 5 weight percent calculated as the oxide and based on the weight of the catalyst composition. Any suitable concentration of the alkali metal, if used, may be utilized in the catalyst composition. Preferably the concentration of the alkali metal is in the range of about 1 to about 10 weight percent and more preferably in the range of about 2 to about 5 weight percent calculated as the oxide and based on the weight of the catalyst composition. If it is desired to use a halogen, any suitable concentration of the halogen may be used. Preferably, the concentration of the halogen is in the range of about 1 to about 10 weight percent and more preferably in the range of about 2 to about 5 weight percent based on the weight of the catalyst composition.

Any suitable cobalt compound may be utilized in the catalyst composition. Suitable cobalt compounds include cobalt acetate, cobalt carbonate, cobalt nitrate, cobalt oxides, and cobalt halides. Any suitable compound of the promoting elements may be utilized in the preparation of the catalyst composition. Suitable zinc compounds include zinc acetate, zinc halides, zinc nitrate, zinc carbonate, and zinc oxide. Suitable titanium compounds include titanium tetrachloride and titanium dioxide. Flame hydrolyzed titanium dioxide is particularly preferred because of its very small particle size. Suitable zirconium compounds which may be utilized in preparing the catalyst composition include zirconium tetrachloride, zirconyl nitrate, zirconyl acetate and zirconium dioxide. Suitable niobium compounds which may be utilized in preparing the catalyst composition include niobium (V) chloride and niobium oxide. Suitable indium compounds which may be utilized in preparing the catalyst composition include indium chloride, indium hydroxide, indium nitrate, indium acetate and indium oxide. Suitable lead compounds which may be utilized in preparing the catalyst composition include lead chloride, lead nitrate, lead acetate, lead carbonate and lead oxides. Suitable bismuth compounds which may be utilized in preparing the catalyst composition include bismuth trichloride, bismuth nitrate, bismuth subnitrate, and bismuth trioxide.

If the alkali metal is used, the alkali metal and phosphorus are preferably added to the catalyst composition as a single compound that contains both the alkali metal and the phosphorus. As an example, if sodium is to be utilized as the alkali metal then the compounds which could be utilized to add the sodium and phosphorus include sodium dihydrogen orthophosphate, disodium monohydrogen orthophosphate, trisodium orthophosphate, and sodium pyrophosphate. The alkali metal and the phosphorus can also be incorporated into the catalyst as separate compounds. Again, utilizing sodium as an example, suitable sodium compounds for use in preparation of the catalyst include sodium hydroxide, sodium carbonate, sodium bicarbonate, sodium sesquicarbonate, sodium nitrate, and sodium acetate. Suitable phosphorus compounds which may be utilized in preparing the catalyst composition, if it is desired to add phosphorus separately from the alkali metal, include orthophosphoric acid, ammonium phosphates, and ammonium hydrogen phosphates.

The oxidative dehydrogenation process of the present invention is preferably carried out by means of an apparatus whereby there is achieved an alternate contact of the catalyst composition with the paraffin to be dehydrogenated and thereafter the catalyst with free oxygen. The process of the present invention is not limited to this type of apparatus and apparatus can be utilized which provide only a continuous contact of the paraffin and free oxygen with the catalyst composition. If a halogen is used, ceramic lined apparatus is preferably used because of the corrosive nature of halogens.

Any suitable oxidative dehydrogenation temperature can be employed which provides the desired degree of catalytic activity in the dehydrogenation of the light paraffins. The oxidative dehydrogenation temperature will generally be in the range of about 480° C. to about 815° C. For the oxidative dehydrogenation of ethane the more preferred temperature is in the range of about 620° C. to about 705° C. The preferred temperature for each of the paraffins which may be oxidatively dehydrogenated in accordance with the present invention decreases below the preferred temperature for the oxidative dehydrogenation of ethane within the broad range of temperature as the carbon number of the paraffin feed increases.

The catalytic oxidative dehydrogenation process can be carried out at any suitable pressure. Below pressures at which the product begins to polymerize, the oxidative dehydrogenation process is not greatly affected by reaction pressure. The pressure of the oxidative dehydrogenation reaction will generally range from about 10 to about 520 kPa and will more preferably range from about 100 to about 200 kPa.

Any suitable feed rate for the feedstock can be utilized. The feedstock may comprise a fluid stream containing either one of the light paraffins or a mixture of the light paraffins and the feed stream may also contain free oxygen. The reactant feed rate expressed as volumes of gas at standard conditions per volume of catalyst per hour (GHSV) will generally range from about 100 to about 2500 with a feed rate of about 500 GHSV being preferred.

If it is desired to introduce a halogen into the process, the halogen may be introduced in any suitable manner. Preferably, the halogen is mixed with the feed stream flowing to the process. Any suitable concentration of the halogen in the feed stream can be utilized. Also continuous or periodic introduction of the halogen in the feed stream can be used. When the halogen is being introduced into the feed stream, the concentration of the halogen is generally maintained in the range of about 20 parts per million to about 10 mole percent with a concentration in the range of about 0.5 to about 4 mole percent being preferred. The halogen can be added to the feed stream in any suitable manner. The preferred form of addition is in the form of a gaseous halogen compound such as the methyl halides.

Any suitable oxidative dehydrogenation reaction time for the cyclic process may be utilized in the oxidative dehydrogenation process. The oxidative dehydrogenation reaction time will generally range from about 0.001 second to about 5 minutes in a cyclic process. The oxidative dehydrogenation cycle preferably will not reduce the cobalt beyond the oxide CoO. Further reduction produces cobalt metal which is not readily regenerated in the presence of free oxygen and causes an irreversible loss of catalyst activity. Consequently it is preferred to keep the dehydrogenation steps sufficiently short that the catalyst does not experience over reduction.

The regeneration of the catalyst may be carried out at the temperature and pressure used in the oxidative dehydrogenation step. The duration of the regeneration step should be sufficient to permit at least the stoichiometric quantity of oxygen required to reoxidize the cobalt to pass over the catalyst. The regeneration time will generally be in the range of about one times the length of the oxidative dehydrogenation step to about ten times the length of the oxidative dehydrogenation step.

The following examples are presented in further illustration of the invention.

EXAMPLE I

Catalyst Preparation

Catalyst A was prepared by combining 21.4 g (0.180 moles) $CoCO_3$, 5.5 g (0.040 moles) $ZnCl_2$, 0.6 g (0.015 moles) of NaOH, and 3 g (0.0113 moles) $Na_4P_2O_7$ in about 50 mL of 4 N $NH_4OH$. The resulting slurry was mixed thoroughly, dried in an oven at about 125° C. and then calcined in air for 3 hours at 815° C. Catalyst A was calculated to contain cobalt, zinc, phosphorus, and sodium in the atomic ratio of about 9:2:1:3, respectively.

Catalysts B and C were prepared by mixing the compound containing the promoter with 16.7 g (0.18 moles) of cobaltous hydroxide and 2.1 g (0.04 moles) of ammonium chloride as a slurry in concentrated aqueous ammonium hydroxide and then adding 3.0 g (0.0067 moles) of $Na_4P_2O_7.10\ H_2O$ and 0.6 g (0.011 moles) of KOH dissolved in water. The resulting slurry was dried in an oven at about 125° C. and then calcined in air for 3 hours at 815° C. followed by 8 hours at 538° C. Catalysts D-E were prepared by mixing the compound containing the promoter with 16.7 g (0.18 moles) of cobaltous hydroxide as a slurry in concentrated aqueous ammonium hydroxide and then adding 3.0 g (0.0067 moles) of $Na_4P_2O_7.10\ H_2O$ and 0.6 g (0.011 moles) of KOH dissolved in water. The resulting slurry was dried in an oven at about 125° C. and then calcined in air for 3 hours at 815° C. followed by 8 hours at 538° C. Table I identifies the promoting element and lists the quantity of promoting compound used in the preparation of catalyst B-E.

TABLE I

| Catalyst | Element | Compound Used |
|---|---|---|
| B | Zirconium | 9.0 g $ZrO(C_2H_3O_2)_2$ |
| C | Bismuth | 19.4 g $Bi(NO_3)_3.5\ H_2O$ |
| D | Niobium | 10.8 g $NbCl_5$ |
| E | Titanium | 7.6 g $TiCl_4$ |

In each of these four preparations the calculated atomic ratio of Co:promoting element:P:Na:K is 9:2:0.7:1.3:0.5.

Catalyst F was prepared by combining 23.8 g (0.20 moles) of $CoCO_3$, 1.6 g (0.02 moles) of $TiO_2$, 1.2 g (0.03 moles) of NaOH, and 2.6 g (0.023 moles) of 85 percent $H_3PO_4$ in about 50 mL of 4 N $NH_4OH$. The resulting slurry was mixed thoroughly, dried in an oven at about 125° C. and then calcined in air for 3 hours at 815° C. followed by 8 hours at 538° C. The calculated atomic ratio of Co:Ti:P:Na was 10:1:1.2:1.5.

Catalyst G was prepared by combining 23.8 g (0.20 moles) of $CoCO_3$, 6.6 g (0.04 moles) of $In(OH)_3$, 1.1 g (0.01 moles) of 85 percent $H_3PO_4$, 0.8 g (0.02 moles) of NaOH, and 0.3 g (0.005 moles) of $NH_4Cl$ in sufficient water to make a thin slurry. The resulting slurry was mixed thoroughly, dried in an oven at about 125° C. and then calcined in air for three hours at 815° C. followed by 8 hours at 538° C. The calculated atomic ratio of Co:In:P:Na was 20:4:1:2.

Catalyst H was prepared by combining 52.4 g (0.18 moles) of $Co(NO_3)_2.6\ H_2O$ and 5.6 g (0.02 moles) of $PbCl_2$ in sufficient aqueous ammonium hydroxide to produce a slurry, then adding 1.0 g (0.01 moles) of 85 percent $H_3PO_4$ and 0.6 g (0.015 moles) of NaOH. The resulting slurry was mixed thoroughly, dried in an oven at about 125° C. and then calcined in air for 4 hours at 704° C. The calculated atomic ratio of Co:Pb:P:Na was 18:2:1:1.5.

Experimental Results

Catalyst A-H were used in runs made in an automated catalyst testing unit as follows: −16+40 mesh catalyst was placed in a quartz reactor and subjected to cyclic operation. A flow of nitrogen was maintained at 500 GHSV throughout the cycles. At 705° C. and atmospheric pressure the catalyst was treated with air flowing at 1000 GHSV for 6 minutes. The flow of air was then shut off while nitrogen purge continued for 3 minutes. Ethane was then introduced into the reactor at 500 GHSV for 3 minutes, followed by a 3 minute purge with nitrogen. The complete cycle (15 minutes in length) was repeated. Product from the 3 minute reaction period with ethane was collected and sampled by gas liquid chromatography analysis at the conclusion of each cycle. Table II presents the measured ethane conversion together with yield and selectivity to ethylene during the runs.

TABLE II

| Catalyst | Cycle No. | $C_2H_6$ Conversion, % | $C_2H_4$ Yield, % | Selectivity to $C_2H_4$, % |
|---|---|---|---|---|
| A | 1 | 80.5 | 68.1 | 84.7 |
| A | 2 | 74.8 | 65.9 | 87.8 |
| A | 3 | 72.2 | 63.8 | 88.3 |
| A | 4 | 68.0 | 59.2 | 86.9 |
| A | 5 | 67.2 | 60.5 | 90.1 |
| A | 6 | 69.1 | 61.5 | 88.9 |
| A | 320 | 58.2 | 44.6 | 76.7 |
| A | 840 | 49.2 | 27.2 | 55.1 |
| B | 1 | 100 | 88.5 | 88.5 |
| B | 25 | 83.3 | 77.9 | 93.5 |
| B | 505 | 31.0 | 20.7 | 66.8 |
| C | 1 | 89 | 78 | 88 |
| C | 50 | 59 | 53 | 90 |
| D | 1 | 95 | 84 | 88 |
| D | 50 | 74 | 68 | 93 |
| E | 1 | 57 | 55 | 95 |
| E | 50 | 53 | 52 | 98 |
| F* | 25 | 24 | 18 | 75 |
| G | 3 | 68 | 63 | 93 |
| G | 129 | 63 | 32 | 50 |
| H | 1–12** | 56 | 33 | 58 |

*Run at 677° C.
**Results are the average of the first 12 cycles.

EXAMPLE II

Catalyst Preparation

Catalyst I was prepared by dissolving 8.9 g (0.030 moles) of $Zn(NO_3)_2.6 H_2O$ in a minimal quantity of water and then adding 1.6 g (0.0139 moles) of 85 percent $H_3PO_4$. To this mixture was added 17.8 g (0.15 moles) of powdered $CoCO_3$, followed by 1.0 g (0.025 moles) of NaOH. After thorough mixing, the resulting material was dried in an oven at about 125° C. then calcined in air for 3 hours at 815° C. Catalyst I was calculated to contain cobalt, zinc, phosphorus, and sodium in the atomic ratio of about 10:2:1:2, respectively.

Catalyst J was prepared exactly like catalyst I except that the addition of NaOH was omitted. Catalyst J was calculated to contain cobalt, zinc, and phosphorus in the atomic ratio 10:2:1, respectively.

Experimental Results

Catalysts I and J were used in runs made in an automated catalyst testing unit in cyclic operation but following a different schedule and different reaction conditions than stated in Example I. These differences and the results from cycles 1, 2 and 5 of the runs are presented in Table III. In these runs no purge with inert gas was used between the dehydrogenation and the regeneration periods of the cycle. The dehydrogenation period was 2.5 minutes; the regeneration period was 6.5 minutes.

One purpose for the runs in Table III was to observe the effect of sodium in the catalyst. Catalyst J, which contained no sodium was considerably more active than catalyst I, but markedly inferior in selectively to ethylene. Yields of oxidation products (CO and $CO_2$) and cracked product (methane) accordingly were higher.

portion of the catalyst was isolated for testing. Catalyst K was calculated to contain cobalt, zirconium, and phosphorus in the atomic ratio 13.5:3:1, respectively. By simple dilution the sodium content of Catalyst K was calculated to be 5 parts per million (0.0005 wt %). Chemical analysis showed the sodium content of catalyst K to be 379 ppm (0.0379 wt %).

Experimental Results

Catalyst K was used in a run in an automated catalyst testing unit as follows. −16+40 mesh catalyst was placed in a quartz reactor and subjected to cyclic operation. A flow of nitrogen was maintained at 500 GHSV throughout the cycles. The catalyst was treated with air for 12 minutes at 1200 GHSV. The flow of air was then shut off while nitrogen purge continued for 1 minute. Ethane was then introduced into the reactor at 500 GHSV for 3 minutes. The flow of ethane was then terminated and the reactor was purged with nitrogen for 3 minutes. The complete cycle (17 minutes in length) was then repeated. Table IV presents results from selected cycles of testing. Tests were at 703° C. and atmospheric pressure.

An examination of the data presented in Table IV illustrates that the low concentrations of sodium which may remain in the catalyst composition when sodium hydroxide is utilized as a precipitating agent do not improve the selectivity of the catalyst composition.

TABLE IV

| Cycle | $C_2H_6$ Conv., % | $C_2H_4$ Yield, % | $C_2H_4$ Selectivity, % |
|---|---|---|---|
| 1 | 48.1 | 21.1 | 43.8 |
| 10 | 44.9 | 20.7 | 46.1 |
| 19 | 43.6 | 19.5 | 44.7 |

TABLE III

| Catalyst | Cycle | Temp., °C. | GHSV, hr$^{-1}$ Air | $C_2H_6$ | $N_2$ | $C_2H_6$ Conv., % | Yields, % CO + $CO_2$ | $CH_4$ | $C_2H_4$ | Sel. to $C_2H_4$, % |
|---|---|---|---|---|---|---|---|---|---|---|
| I | 1 | 676 | 2500 | 500 | 1000 | 17.8 | 1.6 | 0.21 | 16.0 | 89.9 |
| I | 2 | 676 | 2500 | 500 | 500 | 24.8 | 2.9 | 0.50 | 21.4 | 86.4 |
| I | 5 | 703 | 2500 | 500 | 500 | 49.8 | 10.9 | 0.43 | 38.4 | 77.3 |
| J | 1 | 676 | 2500 | 500 | 1000 | 37.9 | 10.9 | 1.27 | 25.8 | 68.3 |
| J | 2 | 676 | 2500 | 500 | 500 | 50.3 | 23.1 | 1.52 | 25.8 | 51.2 |
| J | 5 | 703 | 2500 | 500 | 500 | 84.4 | 51.2 | 1.85 | 31.4 | 38.1 |

EXAMPLE III

Catalyst Preparation

Catalyst K was prepared as follows. 400 mL of an aqueous solution containing 52.4 g (0.18 moles) of $Co(NO_3)_2.6H_2O$ and 10.7 g (0.04 moles) of $ZrO(NO_3)_2.2H_2O$ was added slowly to a stirred beaker containing 500 mL of water. A solution of 2 N NaOH was added concurrently, the solution pH being maintained at 8±0.2. 201 mL of the NaOH solution were used. The resulting solution was filtered and 1.035 liters of filtrate was collected. The resulting filter cake was slurried into 1.066 liters of water. The resulting slurry was then filtered and 1.065 liters of filtrate collected. The resulting filter cake was slurried into 0.521 liters of water. The resulting slurry was filtered and 0.5 liters of filtrate collected. To the resulting filter cake were added 1.55 g (0.0135 mole) of $H_3PO_4$ and 2.13 g (0.04 mole) of $NH_4Cl$ dissolved in a minimum volume of water. After mixing, the resulting mixture was dried in an oven at about 125° C. then calcined in air at 815° C. for 3 hours, and then calcined in air at 538° C. for 8 hours. A −16+40 mesh

EXAMPLE IV

Catalyst B was also used in a run that demonstrated the effect of adding chlorine to the process. A complete process cycle consisted of ethane flowing at 500 GHSV for two minutes followed by air flowing at 1250 GHSV for six minutes. A continuous flow of nitrogen was not used as in Example I. The entire run was made at 675° C. at atmospheric pressure. Periodically, as shown in Table V, gaseous methyl chloride was added to the process. A GHSV of five was sought for the gaseous methyl chloride. However, actual feed rates for the gaseous methyl chloride of up to GHSV=30 were measured because of difficulties in metering the gaseous methyl chloride at the low flow rate. Yields of ethylene from ethane were measured by GLC analysis of snap samples taken at midpoint of the two-minute process cycle. Results through nearly 400 cycles of operation are presented in Table V. Gaseous methyl chloride was added during three periods of the run. During cycles 26-30, 168-201 and 221 gaseous methyl chloride was added to the ethane. During cycles 350-362 gaseous methyl chloride was added to regeneration air but not to the ethane. During each of these intervals the yield of ethylene increased appreciably and then declined when use of methyl chloride was discontinued. It is noted that the effects of introduction of the gaseous methyl chloride do not disappear instantly but rather decrease slowly as the chloride is removed from the catalyst as a volatile compound when the flow of gaseous methyl chloride is terminated.

TABLE V

| Cycle | $C_2H_6$ Conv. % | $C_2H_4$ Yield, % | $C_2H_4$ Selectivity, % | Comment on $CH_3Cl$ |
|---|---|---|---|---|
| 1 | 32.0 | 23.8 | 74.5 | off |
| 10 | 29.0 | 24.7 | 85.0 | off |
| 14 | 28.1 | 27.7 | 88.0 | off |
| 25 | 26.5 | 24.2 | 91.4 | off |
| 26 | 31.3 | 27.4 | 87.4 | on |
| 30 | 57.7 | 45.4 | 78.7 | on |
| 32 | 54.5 | 45.2 | 83.0 | off |
| 36 | 49.4 | 42.6 | 86.3 | off |
| 39 | 34.8 | 31.3 | 89.9 | off |
| 47 | 30.8 | 28.2 | 91.5 | off |
| 166 | 22.1 | 20.5 | 92.9 | off |
| 168 | 25.0 | 23.2 | 92.9 | on |
| 171 | 29.3 | 25.3 | 86.3 | on |
| 174 | 33.6 | 28.7 | 85.3 | on |
| 185 | 47.0 | 38.0 | 80.9 | on |
| 201 | 71.2 | 51.4 | 72.4 | on |
| 204 | 60.9 | 45.4 | 74.5 | off |
| 216 | 46.4 | 37.3 | 80.3 | off |
| 221 | 46.4 | 38.4 | 82.8 | on for this cycle |
| 226 | 44.3 | 37.1 | 83.8 | off |
| 339 | 24.8 | 21.8 | 87.9 | off |
| 350 | | not available | | on, w/air for regeneration |
| 356 | 34.1 | 29.6 | 86.9 | on, w/air for regeneration |
| 362 | 38.7 | 33.3 | 86.2 | on, w/air for regeneration |
| 370 | 34.0 | 30.0 | 88.2 | off |
| 378 | 34.6 | 30.3 | 87.7 | off |
| 386 | 36.6 | 32.1 | 87.8 | off |
| 393 | 36.1 | 31.6 | 87.7 | off |

Reasonable variations and modifications are possible within the scope of the disclosure and the appended claims to the invention.

That which is claimed is:

1. A catalyst composition comprising cobalt; phosphorus; at least one promoter selected from the group consisting of zinc, titanium, zirconium, niobium, indium, lead and bismuth; at least one halogen selected from the group consisting of chlorine, bromine and iodine; and oxygen.

2. A catalyst composition in accordance with claim 1 wherein the atomic ratio of cobalt to said at least one promoter is in the range of about 1:1 to about 20:1, wherein the concentration of phosphorus in said catalyst composition is in the range of about 1 to about 10 weight percent calculated as the oxide and based on the weight of said catalyst composition and wherein the concentration of halogen is in the range of about 1 to about 10 weight percent based on the weight of said catalyst composition.

3. A catalyst composition in accordance with claim 1 wherein the atomic ratio of cobalt to said at least one promoter is in the range of about 3:1 to about 6:1, wherein the concentration of phosphorus is in the range of about 2 to about 5 weight percent calculated as the oxide and based on the weight of said catalyst composition and wherein the concentration of halogen is in the range of about 2 to about 5 weight percent based on the weight of said catalyst composition.

4. A catalyst composition in accordance with claim 1 additionally comprising at least one alkali metal, wherein the concentration of said at least one alkali metal is in the range of about 1 to about 10 weight percent calculated as the oxide and based on the weight of said catalyst composition.

5. A catalyst composition in accordance with claim 4 wherein the atomic ratio of cobalt to said at least one promoter is in the range of about 1:1 to about 20:1, wherein the concentration of phosphorus in said catalyst composition is in the range of about 1 to about 10 weight percent calculated as the oxide and based on the weight of said catalyst composition and wherein the concentration of halogen is in the range of about 1 to about 10 weight percent based on the weight of said catalyst composition.

6. A catalyst composition in accordance with claim 4 wherein the atomic ratio of cobalt to said at least one promoter is in the range of about 3:1 to about 6:1, wherein the concentration of phosphorus is in the range of about 2 to about 5 weight percent calculated as the oxide and based on the weight of said catalyst composition, wherein the concentration of said at least one alkali metal is in the range of about 2 to about 5 weight percent calculated as the oxide and based on the weight of said catalyst composition and wherein the concentration of halogen is in the range of about 1 to about 10 weight percent based on the weight of said catalyst composition.

* * * * *